United States Patent [19]

Jacobsen et al.

[11] 4,250,878

[45] Feb. 17, 1981

[54] NON-INVASIVE CHEMICAL SPECIES DELIVERY APPARATUS AND METHOD

[75] Inventors: Stephen C. Jacobsen; Jerome C. Stenehjem; Robert L. Stephen, all of Salt Lake City; Richard D. Luntz, Murray, all of Utah

[73] Assignee: Motion Control, Inc., Salt Lake City, Utah

[21] Appl. No.: 963,029

[22] Filed: Nov. 22, 1978

[51] Int. Cl.³ .............................................. A61N 1/30
[52] U.S. Cl. ................... 128/207.21; 128/803
[58] Field of Search .................. 128/635, 639–641, 128/644, 172.1, 380, 785, 787, 793, 798, 802, 803, 207.21

[56] References Cited

U.S. PATENT DOCUMENTS

| 750,104 | 1/1904 | Eggers | 128/380 X |
|---|---|---|---|
| 791,730 | 6/1905 | Stanger | 128/172.1 X |
| 1,108,686 | 8/1914 | Bonis | 128/172.1 |
| 2,590,876 | 4/1952 | Landauer | 128/798 |
| 3,590,810 | 7/1971 | Kopecky | 128/640 |
| 3,862,633 | 1/1975 | Allison et al. | 128/641 |
| 4,040,412 | 8/1977 | Sato | 128/641 X |
| 4,141,359 | 2/1979 | Jacobsen et al. | 128/172.1 |
| 4,166,457 | 9/1979 | Jacobsen et al. | 128/172.1 X |

FOREIGN PATENT DOCUMENTS

| 59458 | 6/1913 | Austria | 128/172.1 |
|---|---|---|---|
| 6517113 | 7/1966 | Netherlands | 128/172.1 |
| 19010 | of 1893 | United Kingdom | 128/172.1 |
| 322202 | 2/1972 | U.S.S.R. | 128/172.1 |

Primary Examiner—Lee S. Cohen
Attorney, Agent, or Firm—Thorpe, North, Western & Gold

[57] ABSTRACT

A bioelectrode for non-invasive and inotophoretic delivery of chemical species (such as ions, polar molecules, etc.) into the skin of a person. The bioelectrode includes a pouch having flexible walls, at least a portion of which is composed of a microporous, permeable or semipermeable membrane. The pouch holds fluid which contains the chemical species to be delivered through the skin. An electrode is attached to the pouch so that when the pouch is placed against the skin, with the membrane portion in contact with the skin, and an electric potential is applied to the electrode, chemical species in the pouch are caused to migrate through the membrane and into the skin.

14 Claims, 6 Drawing Figures

NON-INVASIVE CHEMICAL SPECIES DELIVERY APPARATUS AND METHOD

BACKGROUND OF THE INVENTION

This invention relates to a bioelectrode structure and method for delivering chemical species into a person's skin or across the skin barrier.

The use of bioelectrodes for non-invasive delivery of chemical species into or through skin is known. Such bioelectrodes typically include an open receptacle having a generally planar base for holding the fluid to be iontophoresed, one electrode carried within the receptacle for maintaining electrical contact with the fluid, and a second electrode for contacting the skin to produce a potential gradient between the skin and the fluid in the receptacle. Often times the receptacle is fairly rigid to define a rigid perimeter about the opening. The opening in the receptacle is positioned over the skin and then fluid, containing the chemical species, is introduced into the receptacle to contact the skin. When the potential gradient is established, the chemical species migrates into the skin.

Because the prior art receptacles include openings through which the fluid flows to the skin, it is important that a tight seal between the skin and the sealing lip around the opening be maintained to prevent leaking of fluid. This leaking problem is exacerbated when the receptacle must be placed against an especially irregular skin surface because of the difficulty of conforming the typically planar contact base portion of the receptacle with the skin surface. Further, when the receptacle is removed from the skin following an injection, unused fluid may drip from the receptacle opening. This loss of fluid is both wasteful and messy.

It has been suggested that a wicking material be placed over the opening of the bioelectrode receptacle to improve the uniformity of contact between the fluid and the skin surface. Such an arrangement although reducing spillage, does not allow retention and storage of the fluid in the receptacle since, if fluid were introduced into the receptacle long prior to use, the fluid would tend to flow through and evaporate from the wicking material. Also, any substantial pressure on a filled receptacle would tend to accelerate the flow of fluid through and out of the wicking material. See U.S. application Ser. No. 851,082, now U.S. Pat. Ser. No. 4,166,457.

In addition to the above problems, currently used bioelectrodes typically include an electrode element positioned within the receptacle. This configuration insures good electrical contact between the element and the fluid in the receptacle, but introduces another potential source of leakage at the situs in the receptacle wall through which the electrode or electrode connector extends.

Examples of prior art electrodes are described in U.S. Pat. No. 3,862,633, 3,945,384 and 3,973,557. Exemplary prior art apparatus for transferring microorganisms through the skin is disclosed in U.S. Pat. No. 4,100,920.

SUMMARY OF THE INVENTION

It is an object of the invention to provide a method and structurally novel, easy to construct bioelectrode for use in non-invasive and iontophoretic delivery of chemical species into the skin or tissue of a person.

It is another object of the invention to provide such a method and bioelectrode which may be used on irregular skin surfaces.

It is a further object of the invention to provide a bioelectrode constructed to retain fluid in a relatively leak-free manner.

It is still another object of the invention to provide a bioelectrode constructed to facilitate substantially uniform contact with skin surfaces having a variety of shapes.

The above and other objects of the invention are realized in an illustrative embodiment thereof which includes a closed bag or pouch-like member having flexible walls for containing a fluid. At least a portion of the walls of the member is composed of a microporous, permeable or semipermeable membrane through which a chemical species, such as ions, polar molecules, water, etc., contained in a fluid held in the member may diffuse when the membrane is placed against the skin or other tissue of a person and a potential gradient is created between the skin and the fluid. An electrode is carried by the member at a location spaced apart from the membrane to enable creation of such a potential gradient.

This construction facilitates conformation of the member to irregularly shaped skin surface areas so that good contact can be achieved between the membrane and the skin. Provision of the membrane essentially allows retention of the fluid within the member when the member is not in use (even when subject to exterior pressure) and yet allows flow of the fluid therethrough to a person's skin, and when an appropriate potential gradient is created, chemical species are caused to migrate into the skin. In use, the member may be simply pressed against a person's skin, by applying a suitable pressure to the exterior thereof, contact between the skin and the membrane. Use of a pouch-like member with flexible walls facilitates application of pressure at the rear of the member to cause the membrane to make generally uniform contact with the skin regardless of skin surface shapes. No special sealing lip or other sealing structure need be provided.

In accordance with one aspect of the invention, the electrode is mounted on the exterior of the member but in good electrical contact therewith. By mounting the electrode on the exterior rather than interior, a potential source of leakage about the electrode connecting lead which would extend through the wall of the member is eliminated.

BRIEF DESCRIPTION OF THE DRAWINGS

The above and other objects, features and advantages of the present invention will become apparent from a consideration of the following detailed description presented in connection with the accompanying drawings in which.

DETAILED DESCRIPTION

Figure 1:
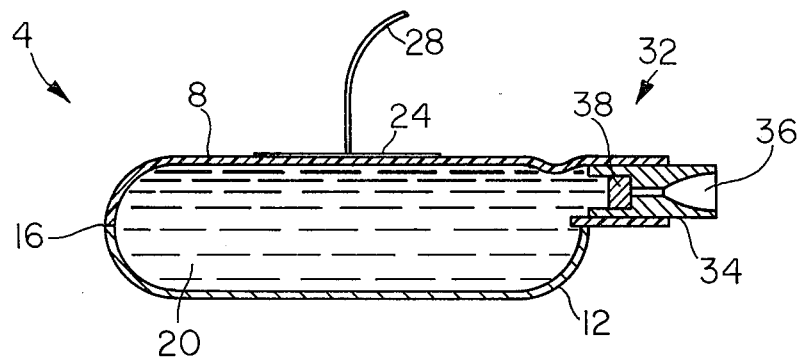
FIG. 1 is a side, cross-sectional view of a bioelectrode made in accordance with the principles of the present invention.
Figure 2:
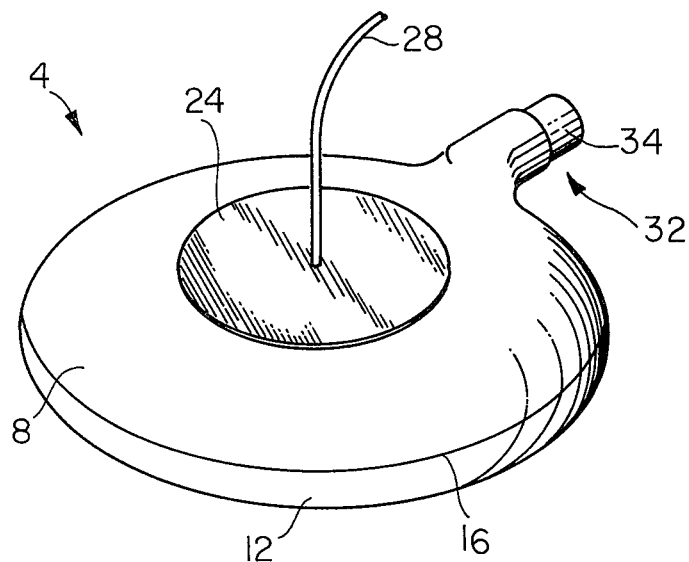
FIG. 2 is a perspective view of the bioelectrode of FIG. 1.

FIGS. 1 and 2 respectively show a side, cross-sectional view and a perspective view of a device for use in non-invasive delivery of fluid through the skin of a person.

The device includes a pouch or bag 4 having two generally facing walls 8 and 12. The walls are joined at their perimeter 16 as shown in the drawings. Both walls 8 and 12 are constructed of flexible, deformable material to allow the pouch 4, and in particular the bottom wall 12, to conform to and uniformly contact a variety of irregularly shaped surfaces. The bottom wall 12 is composed of a microporous, permeable or semipermeable membrane material such as microporous polycarbonate, microporous polytetrafluoroethylene or polyacrylonitrile. This material is flexible and will function to contain fluid within the pouch 4 until subjected to certain operating conditions to be described momentarily. The top wall 8 may be composed of polyurethane or other flexible material. The pouch 4 is closed (free of openings) to retain a solution 20 containing a chemical species which is for delivery into the skin.

Mounted on the exterior of the top wall 8 is an electrode plate 24. The electrode plate 24 extends over a substantial portion of the top wall 8 and is attached in such a way as to maintain electrical contact with the wall. An adhesive or strap may be used to attach the electrode. Electrically coupled to the electrode plate 24 is a conductor 28 leading to an electric potential source (not shown).

Advantageously, the electrode plate 24 is constructed of flexible materials such as a thin sheet of stainless steel so that the plate will not inhibit deformation of the pouch 4. In this manner, substantially all of the pouch walls are deformable and flexible as desired.

As can be seen from the drawings, the walls 8 and 12 of the pouch 4 present generally planar or convex exterior surfaces. Such construction facilitates a snug, generally uniform contact between the pouch and a skin surface area against which the pouch is placed, regardless of the shape of the skin surface. Further, pressure may be applied to the top wall 8 of the pouch to force the bottom wall 12 to better conform to the skin surface against which it is placed and since there are no openings in the pouch, the fluid will not leak from the pouch. Such so-called rear "loading" of the pouch 4 produces hydrostatic pressure within the pouch which forces the membrane 12 into substantially uniform contact with the skin surface. With such contact, more rapid transfer of the chemical species into the skin can be achieved.

Use of a semipermeable membrane enables control of the chemical species allowed to pass through the membrane. For example, a polyacrlonitrile membrane passes lidocaine hydrochloride ions and blocks passage of large protein molecules. Use of a membrane having openings of about 0.22 microns or less will allow passage of ions generally but block passage of bacteria of almost any kind.

It may be desirable to form on one side of the pouch 4 and in the top wall 8 an injection channel 32 through which fluid could be introduced into the pouch 4. This channel could be similar to that disclosed in copending patent application, Ser. No. 851,082, now U.S. Pat. Ser. No. 4,166,457 and is described in detail there. Briefly, the channel 32 includes a tubular member 36 which defines an orifice 36 for receiving a cannula. A self-sealing plug 38 is disposed at the end of the orifice 36 to block access to the interior of the pouch 4. Fluid is introduced into the pouch by inserting a cannula into the orifice 36 and then forcing the tip of the cannula through the plug 38. The fluid is then transferred through the cannula and into the pouch 4. Upon removal of the cannula, the plug seals and prevents outflow of fluid from the pouch.

Although a particular injection channel arrangement has been described, it should be understood that a variety of arrangements could be utilized to introduce fluid into the pouch 4 and, in fact, the pouch could be manufactured without any injection channel, with the fluid being introduced at the time of manufacture.

In use, the pouch 4 containing a solution with a selected chemical species such as lidocaine hydrochloride is placed against a person's skin with the membrane 12 (such as polyacrylonitrile) making contact with the skin. Another electrode (not shown) is placed against the skin at a location spaced from the pouch. A pressure is applied to the back wall 8 of the pouch to force the membrane 12 into substantially uniform contact with the skin. Appropriate electric potentials are applied to the electrode 24 and the other electrode (not shown) to create a potential gradient between the electrode 24 and the skin. In effect, the electrode 24 produces an electric field, which causes migration of the chemical species (e.g. ions, polarized particles, etc.) toward and through the membrane 12. The ions are also caused to migrate into the skin to provide a noninvasive introduction of the ions into the skin as desired.

Figure 3:
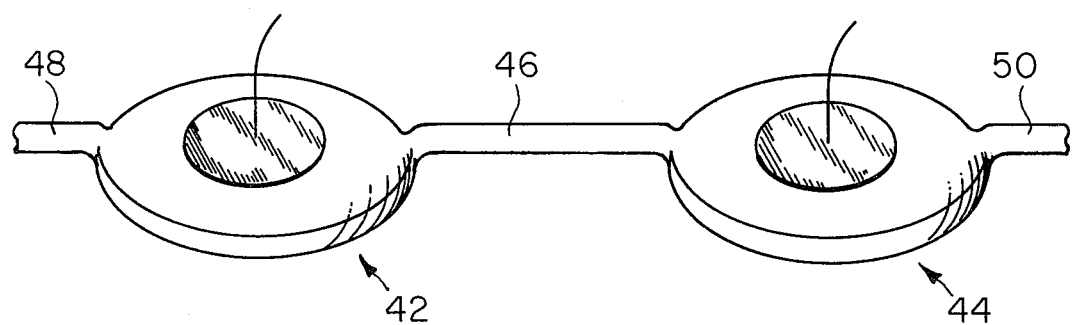
FIG. 3 is a perspective view of a pair of bioelectrodes joined together.

FIG. 3 shows a pair of pouches 42 and 44, each constructed similar to the construction of the pouch of FIGS. 1 and 2, but without the injection channel. The pouches 42 and 44 are joined together by a flexible strap or tether 46 and, as indicated in the drawing, other pouches could be attached to those shown by additional straps 48 and 50.

The pouches 42 and 44 contain chemical species to be delivered into the skin of a person at spaced-apart locations. A third electrode (not shown) would be used with the pouches 42 and 44 to produce a potential gradient suitable for causing migration of the chemical species into the skin.

Figure 4:
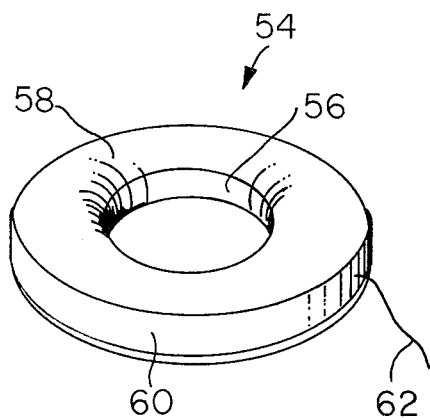
FIG. 4 is a perspective view of a bioelectrode made in accordance with the present invention in the form of an annulus.

FIG. 4 shows a bioelectrode formed in the shape of an annulus 54. This bioelectrode includes an exterior wall 58 constructed, for example, of a flexible, deformable material similar to that of the top wall 8 of the FIGS. 1 and 2 device. An interior wall 56 (interior of the opening in the annulus 54) is constructed of a microporous, permeable or semipermeable membrane material similar to that of the bottom wall 12 of the device of FIGS. 1 and 2. The annulus 54 is hollow for holding a chemical species to be delivered into the skin of a person.

An electrode plate 60 is disposed about and attached to the exterior circumference of the annulus 54 as shown. A conductor 62 couples the plate 60 to an electric potential source (not shown).

The device of FIG. 4 would be used on body parts about which the device could be placed such as appendages. The appendage would be inserted through the opening in the annulus 54 so that the interior wall 56 was in contact with the skin, and then an electric potential would be applied to the electrode plate 60 and to another electrode (not shown) placed against the skin.

Figure 5:
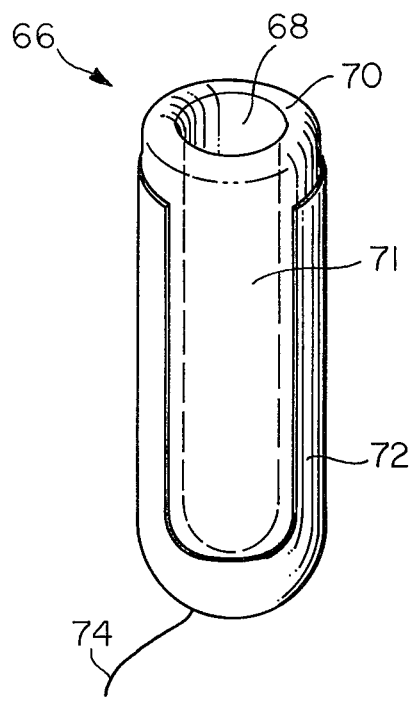
FIG. 5 is a perspective view of a bioelectrode made in accordance with the present invention in the form of a cylinder.

Still another embodiment of the present invention, in the form of a cylinder, is shown in FIG. 5. The bioelectrode of FIG. 5 includes a cylindrical pouch 66 having an interior wall 68 constructed of a microporous, permeable or semipermeable membrane material. An exterior wall 70, spaced from the interior wall, is constructed of any suitable material for retaining a solution. The pouch 66 has an opening in the tip thereof for receiving a body part such as a finger. The bottom of the pouch 66 is closed as indicated by the dotted line 71 representing the interior wall.

An electrode plate 72 is formed to fit about and attach to a portion of the exterior wall 70. An electrical conductor 74 is coupled to the plate 72 for connecting the plate to an electric potential source.

Figure 6:
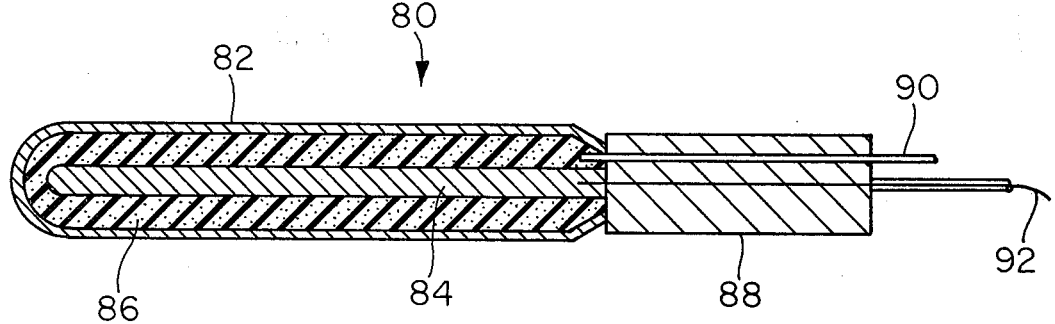
FIG. 6 is a partially cross-sectional view of a bioelectrode made in accordance with the present invention in the form of an elongate finger.

FIG. 6 shows a partially cross-sectional view of an elongate bioelectrode 80 for inserting into body cavities or orifices. This bioelectrode includes an electrode rod 84 surrounded by sponge or other resilient porous material 86. Surrounding and enclosing both the rod 84 and the material 86 is a pouch 82 composed of a microporous, permeable or semipermeable material. A handle 88 is mounted on one end of the rod 84 and attached to the pouch 82 to close off and to aid in manipulation of the pouch. A tube 90 for injecting fluid to the pouch 82 extends from within the pouch through the handle to the back end thereof. An electrical conductor 92 is coupled to the rod 84 and extends through the handle 88 and out the back for coupling to an electric potential source.

The material 86 is provided to cushion and prevent the pouch 82 from contacting and rubbing against the rod 84. Also, the material 86, being resilient, tends to force the walls of the pouch 82 outwardly to thereby tend to place the exterior surface of the walls in better contact with the walls of any body cavity or orifice into which the pouch is inserted. The rod serves both as the electrode element of the device and as a stiffening member to facilitate inserting the pouch 82 into a body cavity.

A simple, convenient and easy to use bioelectrode has been described. The basic elements of the bioelectrode, in whatever form it takes, are a pouch having flexible walls, at least a portion of which is composed of a microporous permeable or semipermeable membrane suitable for passing ions or other charged or polarized particles of a fluid, and an electrode carried by the pouch. In use, the pouch is pressed against the skin so that a generally uniform contact between the skin and the membrane is achieved.

It should be understood that the above-defined embodiments are only illustrative of the application of the present invention and that numerous other alternative embodiments could be described without departing from the spirit and scope of the invention. For example, the pouch holding the fluid could take a variety of shapes and sizes and the electrode carried by the pouch could be secured either on the exterior or interior thereof. The appended claims are intended to cover all described embodiments and alternative embodiments which the present invention might have.

What is claimed is:

1. A bioelectrode for use in the iontophoretic delivery of a chemical species into the skin or tissue of a person comprising
   a pouch for holding a fluid containing the chemical species, said pouch including flexible and deformable walls adapted to generally conform to surface shapes against which they are placed, at least a portion of which includes a microporous membrane separating the interior of the pouch from the exterior and having openings of about 0.22 microns or less in diameter, said portion being formed to present a generally planar to convex exterior surface, and
   an electrode carried by said pouch for coupling to an electric potential source.

2. A bioelectrode as in claim 1 wherein said electrode is mounted on the exterior surface of said walls in electrical contact therewith and spaced from said membrane.

3. A bioelectrode as in claim 2 wherein said electrode is formed of a flexible conductive material.

4. A bioelectrode as in claim 1 further comprising
   a second pouch for holding a fluid containing additional chemical species, said second pouch including flexible and deformable walls adapted to generally conform to surface shapes against which they are placed, at least a portion of which includes a microporous membrane separating the interior of the second pouch from the exterior and having openings of about 0.22 microns or less in diameter, said portion of said second pouch being formed to present a generally planar to convex exterior surface,
   a second electrode carried by said second pouch for coupling to an electric potential source, and
   flexible means coupling the first-mentioned and second pouch together.

5. A bioelectrode as in claim 1 wherein said pouch is formed in the shape of an annulus and wherein said membrane is disposed about the interior circumference of the annulus.

6. A bioelectrode as in claim 5 wherein said electrode is attached to the exterior surface of said pouch to extend about the exterior circumference of said annulus.

7. A bioelectrode as in claim 1 wherein said pouch is formed in the shape of an elongate bag, and wherein said electrode is formed in the shape of a rod disposed within said bag.

8. A bioelectrode as in claim 7 further including a porous, resilient material disposed between said electrode and the interior surface of the pouch walls.

9. A bioelectrode as in claim 1 wherein said pouch is formed in the shape of a cylinder in which said walls are positioned concentrically.

10. A bioelectrode as in claim 9 wherein said electrode is attached to the exterior surface of said pouch.

11. A bioelectrode as in claim 1 further comprising channel means formed in said pouch to enable introduction therethrough of fluid into said pouch.

12. A bioelectrode for use in the iontophoretic delivery of a chemical species into the skin or tissue of a person comprising
   a pouch for holding a fluid containing the chemical species, said pouch including a first flexible and deformable wall portion constructed of a semipermeable membrane having openings of about 0.22 microns or less in diameter, said first wall portion being adapted to allow passage therethrough of certain ions and molecules but to block passage of certain other molecules, and a second flexible and deformable wall portion disposed in a generally facing relationship with said wall portion, and
   an electrode carried by said pouch for coupling to an electric potential source.

13. A bioelectrode as in claim 12 wherein said electrode is mounted on the exterior surface of said second wall portion in electrical contact therewith.

14. A method of non-invasively delivering chemical species into the skin or tissue of a person comprising, placing against the skin or tissue a pouch holding a fluid containing said chemical species, said pouch having flexible walls, one of which consists of a microporous or semipermeable membrane which is positioned in contact with the skin or tissue, applying pressure to said pouch to cause that portion of the pouch in contact with the skin or tissue to conform to the surface shape of the skin or tissue, applying a first electric potential to a portion of the skin or tissue spaced from the location of contact of said pouch, and applying a second electric potential to an exterior surface of said pouch to cause the migration of the chemical species through said membrane and into the skin or tissue.

* * * * *